United States Patent [19]

Pollack

[11] 3,947,250

[45] Mar. 30, 1976

[54] METHOD OF IMMUNODIFFUSION

[75] Inventor: Vincent A. Pollack, Annaheim, Calif.

[73] Assignee: Baxter Laboratories, Inc., Deerfield, Ill.

[22] Filed: June 21, 1974

[21] Appl. No.: 481,621

[52] U.S. Cl. ........ 23/230 B; 195/103.5 R; 252/316; 252/408; 424/12

[51] Int. Cl.[2] A61K 37/00; B01J 13/00; G01N 31/02; G01N 33/16

[58] Field of Search ...................... 23/230 B, 259, 292; 252/316, 408; 424/8, 12, 13; 195/103.5 R

[56] References Cited

UNITED STATES PATENTS

| | | | |
|---|---|---|---|
| 2,773,801 | 12/1956 | Fox | 260/615 B |
| 3,389,966 | 6/1968 | Saravic | 23/230 B |
| 3,709,661 | 1/1973 | Hubscher | 252/408 X |
| 3,725,004 | 4/1973 | Johnson et al. | 23/259 X |
| 3,736,100 | 5/1973 | Rains | 23/230 B X |

OTHER PUBLICATIONS

McCutcheon's Detergent and Emulsifiers D&E 1973, p. 129.

Immumology as a Laboratory Tool JAMA Vol. 37, No. 12 p. 455–469.

A General Method of Increasing the Sensitivity of Immune Diffusion Clin. Chem. Acta 38 (1972) 329–337.

*Primary Examiner*—Joseph Scovronek
*Assistant Examiner*—Michael S. Marcus
*Attorney, Agent, or Firm*—Louis A. Altman; Lawrence W. Flynn; Max D. Hensley

[57] ABSTRACT

A method of immunodiffusion for determination of proteins of low concentration in biological fluids employing a gel medium containing 2.5–5% block copolymer of ethylene oxide and polyoxypropylene polymer.

9 Claims, No Drawings

METHOD OF IMMUNODIFFUSION

This invention relates to a method for the quantitation of proteins which are of extremely low concentration in blood serum and other biological fluids. More particularly, this invention relates to a method of enhancing the visibility of precipitin zones in immunodiffusion reactions.

Within recent years various new immunological techniques have been developed for the determination of serum proteins. One of the most important of these contributions to the quantitation of serum protein components has been the development of the single diffusion type of precipitin reaction. In particular, the term radial immunodiffusion has been applied to a system in which one of two immune reactants, usually antibody, is incorporated in a semi-solid gel such as agar in which the gel is spread out on a surface and the other immune reactant, generally antigen, is allowed to diffuse radially from a circular reservoir. In this procedure, the antigen diffuses radially out of the reservoir or well punched in the gel into the surrounding gel-antibody mixture, and a visible disc or ring of precipitate (precipitin ring) forms where the antigen and antibody have reacted. The diameter of the precipitin zone formed is directly proportional to the amount of antigen present in the test serum and inversely proportional to the concentration of antibody incorporated in the gel.

Further description of the radial immunodiffusion technique is provided by Mancini, *Immunochemistry*, Vol. 2, pp. 235–254 (1965) and Lou and Shanbrom, *JAMA*, Vol. 200, No. 4, p. 323 (1967).

The techniques of radial immunodiffusion have been applied to the determination of serum proteins such as prealbumin, albumin, $\alpha_1$-antitrypsin, $\alpha_2$-macroglobulin, ceruloplasmin, transferrin, C3($\beta$1A/C), and the immunoglobulins (IgA, IgM, IgG, and IgD). Peetoom, *Amer. J. of Med. Tech.*, Vol. 37, No. 12, December 1971.

IgE is the most recently discovered class of immunoglobulins which possess antibody activity. It has a molecular weight of 184,500 (7.9S) and constitutes the smallest portion of serum immunoglobulins with a normal adult range of 15 to 800 IU/ml (means about 200 IU/ml). Bazaral et al. *J. Immunol.*, Vol. 107, pp. 794–801 (1971); Jacobs et al. *Lancet*, Vol 2, pp. 1059–61 (1972). IU/ml is defined by Rowe et al. *Bull. Wld. Hlth. Org.*, Vol. 43, pp. 609–11 (1970). See also Anderson et al. *Clin. Chim. Acta*, Vol. 36(1), pp. 276–81 (1972).

Due to the extremely low concentration of IgE in blood serum, the precipitin rings produced by the IgE antigen-antibody reaction in conventional radial immunodiffusion are only difficulty visible. In accordance with the present invention the visibility of these diffusion rings is markedly enhanced when testing for IgE and similar such proteins of low concentration.

Briefly stated, the present invention comprises incorporating in the immunodiffusion gel medium a small but effective amount of from about 0.5 to about 5% by weight of the medium of block copolymer of ethylene oxide and polyoxypropylene polymer.

The block copolymers employed in this invention can be represented by the formula $HO(C_2H_4O)_b(C_3H_6O)_a(C_2H_4O)_bH$ wherein $a$ is an integer such that the hydrophobe base represented by $(C_3H_6O)$ has a molecular weight of at least 950 and $b$ is an integer such that the hydrophile portion represented by $(C_2H_4O)$ constitutes from about 50 to about 90% by weight of the compound. These compounds can be prepared by condensing ethylene oxide with polyoxypropylene polymer. A further description of the preparation of these block copolymers is found in U.S. Pat. No. 2,674,619.

Illustrative examples of suitable block copolymers for practice of the present invention are the F-38 and F-68 "PLURONIC" polymers commercially available from the Wyandotte Chemicals Corporation. F-38 contains 80% of polyoxyethylene hydrophilic units in the molecule and the polyoxypropylene hydrophobic base has a molecular weight of 950. F-68 also contains 80% of polyoxyethylene hydrophilic units in the molecule but the hydrophobic base has a molecular weight of 1750. The total molecular weights of these two "PLURONIC" polyols is 4750 and 8750, respectively. A further description of these polyols is found in the bulletin of Wyandotte Chemicals Corporation, "The Pluronic Grid", Sixth Edition, which is incorporated herein by reference.

The block copolymers employed in this invention are distinguished from the polyethylene glycol polymers used in immunodiffusion reactions in accordance with Harrington et al., *Immunochemistry*, Vol. 8, pp. 413–21 (1971); Darcy, *Clin. Chim. Acta*, Vol. 38, pp. 329–37 (1972); and Lundkvist and Ceska, *Immunology*, Vol. 23, pp. 413–22 (1972). While polyethylene glycol tends to enhance the visibility of precipitin zones in immunodiffusion reactions, it also at the same time undesirably increases the non-specific precipitation whereby the clarity of the precipitin zone is reduced. In accordance with the present invention it has been found that the block copolymer as defined herein produces precipitin rings which are significantly and substantially clearer and more distinct than those obtained with polyethylene glycol.

In the preparation of the gel medium used in accordance with this invention, conventional gelling agents are used such as, for example, gelatin, pectin, silica gel, starch, polysaccharides from seaweeds such as agar, agarose, algin and carrageenin, synthetic polymeric gelling agents such as the cross-linked polyacrylamide disclosed in U.S. Pat. No. 3,046,201, the modified celluloses disclosed in U.S. Pat. No. 3,360,440, the modified agars and agaroses described in British Pat. No. 1,350,024, and the like materials. The gelling agent preferably has the physical properties characterizing agar-agar insofar as it is readily dispersible in hot water and capable of forming an essentially clear hydrogel of sufficient rigidity so that the receptacle or plate containing the gel can be inverted without danger of the gel falling out.

Agarose is the preferred gelling agent employed in the gel medium of the present invention. Agarose is the neutral galactose polymer which has been separated from the agaropectin fraction of agar by any conventional method, for example, a method such as described in U.S. Pat. Nos. 3,281,409; 3,335,127; and 3,362,884. Agar such as that commercially available from Difco Laboratories under the tradename "Noble" agar and mixtures of agarose and agar also are suitable for use in the present invention.

The gelling agent generally is employed in concentrations of from about 0.1 to about 5% by weight of the gel medium. Preferably, about 0.5 to about 1.5% by weight of agarose is employed.

The gel medium of this invention also generally employs a buffer system to maintain an essentially constant hydrogen ion concentration. Any conventional buffer system can be employed, for example, phosphate, acetate, borate, citrate, tris-(hydroxymethyl-)aminomethane-glycine, tris-EDTA, barbital and the like buffer systems. Preferably, a glycinesaline buffer, pH 8.0–8.5, such as described in U.S. Pat. No. 3,088,875, is employed.

Various diluents such as bovine serum albumin, fetal calf serum and various preservatives such as sodium azide, merthiolate and the like can also be employed in the gel medium in conventional amounts.

The following examples will further illustrate the invention although it will be understood that the invention is not limited to these specific examples.

EXAMPLE 1

An immunodiffusion plate for the determination of IgE is prepared as follows:

Preparation of Reagents

A. Glycine-saline buffer

| | | |
|---|---|---|
| Glycine | 0.1M | 7.5g/liter |
| NaCl | 0.15M | 9.0g/liter |

Adjust pH to 8.2 with N NaOH

B. Agarose solution

To 100 ml. glycine-saline buffer prepared above add one gram agarose and two grams "PLURONIC" F-38 polymer and heat to form a clear solution of 1% agar and 2% polymer.

C. Antibody

IgE antibody is obtained by immunization of horses with IgE antigen followed by periodic bleedings to a predetermined suitable IgE antibody titer.

Procedure

The foregoing reagents are admixed in suitable proportions with heating to provide a solution having a final concentration as follows:

| Reagent | Concentration |
|---|---|
| IgE antibody | About 1:200 (antibody:buffer) dilution in the buffer |
| Agarose | 0.90% |
| "PLURONIC" F-38 | 1.8% |
| Glycine | 0.09M |
| NaCl | 0.135M |

The above solution is poured into the recess of an immunodiffusion plate such as described in U.S. Pat. No. 3,725,004 and illustrated in FIGS. 1 to 5 therein. The solution is allowed to gel and six wells of 5 mm diameter each are then punched in the gel, one well being centrally located in each of six scalloped diffusion zones.

The radial immunodiffusion test for IgE is performed by filling one of the wells with a reference serum containing a suitable dilution of IgE antibody. The remaining five wells are filled with test serum specimens. A plastic cover is placed over the immunodiffusion plate and the plate incubated for 48 hours at 37° C in a moist chamber. At the end of the incubation period the plate is observed for the formation of precipitin rings. The plate is then overlaid with an aqueous solution of 7.5% acetic acid as a staining technique and the precipitin rings are again observed. The precipitin ring diameters are determined and the square of the mean precipitin ring diameter is calculated by conventional means. The concentration of IgE is then determined by reference to a standard curve which plots the mean precipitin diameter on the ordinate axis and the IgE in IU/ml on the abscissa axis.

The foregoing example was repeated except that 3% polyethylene glycol 4000 was employed in the agar solution instead of the 2% "PLURONIC" F-38. It was found that the visiblity of the precipitin rings of the foregoing example with the "PLURONIC" F-38 were markedly enhanced in that they were significantly and substantially clearer and more distinct than those obtained with the polyethylene glycol.

EXAMPLE 2

Example 1 is repeated except that a mixture of 0.80% agarose and 0.40% agar is used in place of the 0.90% agarose with substantially similar results.

EXAMPLE 3

Example 1 is repeated except that "PLURONIC" F-68 is employed in the agar solution instead of "PLURONIC" F-38 with substantially similar results.

EXAMPLE 4

Example 1 is repeated four times except that equivalent amounts of IgA, IgM, IgG and IgD, respectively, are each substituted for the IgE antibody with substantially similar results.

In the foregoing, the dilution of the IgE antibody in buffer can vary widely, depending upon the IgE titer in the horse antiserum which, of course, is dependent upon the horse. Other species can also be used as suitable sources of IgE antibody. In general, dilution of about one part of antibody in about 100 to 300 parts of buffer is suitable for purposes of the present invention although it will be understood that the invention is not limited to this range of antibody in the gel.

Various other examples and modifications of the foregoing examples will be apparent to the person skilled in the art after reading the foregoing specification without departing from the spirit and scope of the invention and it is intended to include all such further modifications and examples in the appended claims.

What is claimed is:

1. In the method of immunodiffusion employing an aqueous gel medium containing from about 0.1 to about 5% by weight of a gelling agent for the determination of low levels of protein diffusion of said protein in said gel medium, the improvement comprising incorporating in the gel medium in order to enhance visibility of diffusion rings when testing for proteins of low concentration from about 0.5 to about 5% by weight of the medium of a block copolymer having the formula $HO(C_2H_4O)_b(C_3H_6O)_a(C_3H_4O)_bH$ wherein $a$ is an integer such that the hydrophobe base represented by $(C_3H_6O)$ has a molecular weight of at least 950 and $b$ in an integer such that the hydrophile portion represented by $(C_2H_4O)$ constitutes from about 50 to about 90% by weight of the compound.

2. The method of claim 1 in which the protein is IgE antibody.

3. The method of claim 1 in which the block copolymer contains about 80% polyoxyethylene hydrophilic units in the molecule and the polyoxypropylene hydrophobe has a molecular weight of about 950.

4. The method of claim 1 wherein the gel medium is incubated during diffusion of said protein in said gel medium, and after incubation the gel medium is stained with aqueous acetic acid solution.

5. A composition of matter for use with an immunodiffusion plate for the determination of low levels of protein concentration in blood serum comprising a gel medium containing a predetermined amount of antigen or antibody, from about 0.1 to about 5% by weight of a gelling agent selected from the group consisting of agar, agarose, and mixtures thereof, and from about 0.5 to about 5% by weight of a block copolymer having the formula $HO(C_2H_4O)_b(C_3H_6O)_a(C_2H_4O)_bH$ wherein *a* is an integer such that the hydrophobe base represented by $(C_3H_6O)$ has a molecular weight of at least 950 and *b* is an integer such that the hydrophile portion represented by $(C_2H_4O)$ constitutes from about 50 to about 90% by weight of the compound.

6. The composition of matter of claim 5 which contains a predetermined amount of IgE antibody.

7. The composition of matter of claim 5 in which the block copolymer contains about 80% polyoxyethylene hydrophilic units in the molecule and the polyoxypropylene hydrophobe has a molecular weight of about 950.

8. The composition of matter of claim 5 in which the gelling agent is agarose.

9. The composition of matter of claim 8 in which the concentration of agarose is from about 0.5 to about 1.5% by weight.

* * * * *

UNITED STATES PATENT AND TRADEMARK OFFICE
CERTIFICATE OF CORRECTION

PATENT NO. : 3,947,250

DATED : March 30, 1976

INVENTOR(S) : Vincent A. Pollack

It is certified that error appears in the above-identified patent and that said Letters Patent are hereby corrected as shown below:

Claim 1, line 10, "$HO(C_2H_4O)_6$" should be --$HO(C_2H_4O)_b$--

Signed and Sealed this

*Seventeenth* Day of *January 1978*

[SEAL]

*Attest:*

RUTH C. MASON
*Attesting Officer*

LUTRELLE F. PARKER
*Acting Commissioner of Patents and Trademarks*